United States Patent [19]

Bailey

[11] Patent Number: 5,484,284
[45] Date of Patent: Jan. 16, 1996

[54] DENTAL PROPHYLAXIS TOOL AND ANGLE USING IT

[75] Inventor: Ronald L. Bailey, Harvester, Mo.

[73] Assignee: Young Dental Manufacturing Company, Inc., Earth City, Mo.

[21] Appl. No.: 281,765

[22] Filed: Jul. 28, 1994

[51] Int. Cl.$^6$ ..................................................... A61C 3/06
[52] U.S. Cl. .......................................... 433/125; 433/166
[58] Field of Search ..................................... 433/125, 166

[56] References Cited

U.S. PATENT DOCUMENTS

| | | | |
|---|---|---|---|
| 1,837,938 | 12/1931 | Young | 433/166 |
| 2,451,918 | 10/1948 | Chott | 433/166 |
| 3,407,502 | 10/1968 | Richmond . | |
| 3,436,830 | 4/1969 | Richmond . | |
| 3,478,433 | 11/1969 | Richmond | 433/166 X |
| 3,789,462 | 2/1974 | Reich | 433/166 |
| 4,253,832 | 3/1981 | Bailey . | |
| 4,292,027 | 9/1981 | Richmond . | |
| 4,365,956 | 12/1982 | Bailey | 433/125 X |
| 5,178,538 | 1/1993 | Eckert | 433/125 X |

Primary Examiner—Nicholas D. Lucchesi
Attorney, Agent, or Firm—Polster, Lieder, Woodruff & Lucchesi

[57] ABSTRACT

A prophylaxis cup is provided to be used with a dental prophylaxis angle. The cup includes an elastomeric body having an upper section and a lower section and a threaded shaft extending axially from the lower section. The shaft has a head embedded in the body's lower section. The lower section has a deformable annular ring concentric with, and adjacent to, the shaft head. The ring is deformable outwardly into an adjacent annular groove radially outboard of the ring. A peripheral slinger or skirt outboard of the groove extends downwardly and away from the groove. The cup's body upper section defines a pocket which receives cleaning abrasives. When the cup's shaft is threaded into a rotatable driven gear on the dental prophylaxis angle, a stationary edge of a hollow cap stem on the angle engages the cup's ring, to form a rotational ring seal. The structure of the cup ensures that the seal is maintained even when the cup is bent or deformed during use.

23 Claims, 2 Drawing Sheets

DENTAL PROPHYLAXIS TOOL AND ANGLE USING IT

BACKGROUND OF THE INVENTION

This invention relates to tools for use with dental prophylaxis angles, and in particular, to a prophylaxis cup which will provide a better seal with the angle to prevent abrasive and other foreign material from entering the angle.

Prophylaxis (prophy) cups are used by dentists or dental hygienists to polish a patient's teeth with paste carried by the rotating cup. The cup is mounted on the driven gear of a prophylaxis (prophy) angle. The prophy angle includes a body having a head carrying the driven gear and a tubular part carrying a drive gear including a shaft. The tubular body of the prophy angle is held on the nose of a motorized handpiece, and the drive shaft is gripped by a rotatable collet in the handpiece.

If the abrasive polishing paste or other foreign material enters the angle during a cleaning procedure, it can cause premature wear of the gears and their bearings. Moreover, mixtures of abrasive paste and saliva are difficult to clean out of the angle, and unless the angle is properly autoclaved it is a potential source of cross contamination.

To prevent foreign matter from entering the angle, most angles include an internal seal. When the seal wears, however, internal contamination of the angle occurs and expensive repairs are required. An alternative approach was suggested by George Richmond in a series of patents (U.S. Pat. Nos. 3,407,502, 3,436,830, 3,478,433, and 4,292,027) which disclose using the rubber prophy cup itself as the seal. This approach assures that a new seal is formed every time a new cup is placed on the prophy angle to perform a dental prophylaxis procedure. As shown in U.S. Pat. No. 3,478,433, it is possible to make a cup which forms a first seal with a knife edge at the end of a sleeve portion of a cap on the prophy angle, a second seal with a side of the sleeve portion, and a third seal (or slinger) with a peripheral portion of the cap. A commercial embodiment of such a sealing prophy cup is sold by Young Dental Manufacturing Company of Earth City, Mo., under the registered trademark TRIPLE SEAL. This cup is shown in FIG. 1 of the drawings. The cup 1 seals against the stem 3 of the angle's cap 5 at two points S1 and S2. Seal point S1 is a compression seal between the cup and the knife edge of the cap stem 3. As the cup 1 rotates, the knife edge cuts into the rubber cup and compresses the rubber outwardly. Seal point S2 is a ring seal which is formed by an inwardly directed annular rib 7 which seals against the side of the stem. A slinger or skirt 9 forms the third seal and functions to direct contaminants away from the opening in the cap 5.

The cup 1 has been found to work quite well. However, the multiple rubbing seals with the cap stem produce a large amount of friction. This friction causes the cup and prophy angle to heat up quickly and requires a greater amount of torque to run the cup than would be needed if the frictional engagements were reduced. Further, when shearing forces are applied to the cup, such as when the cup is pulled across a patient's tooth, the cup bends laterally. The bending of the cup causes the rib 7 and the seals S1 and S2 to pull away from the stem. This tends to break the seals and allow liquids and abrasives to enter the handpiece.

SUMMARY OF THE INVENTION

One object of the present invention is to provide a prophy cup which will substantially prevent contaminants from entering a prophy angle.

Another object is to provide such a prophy cup which can be operated at a low torque.

Another object is to provide such a prophy cup which produces a minimum amount of friction in sealing the angle.

Another object is to provide a cup which forms a seal which will be maintained even when the cup is distorted, such as by shear forces, during use.

Another object is to provide such a prophy cup which is inexpensive to produce.

Other objects will become apparent to those skilled in the art in light of the following description and accompanying drawings.

Briefly stated, a prophylaxis tool is provided to be used with a dental prophylaxis angle. The tool includes a body having an upper section, a lower section, and a threaded shaft or screw. The threaded shaft extends from the bottom of the tool. The tool's lower section has a deformable annular ring concentric with the shaft head. The ring is defined by the inner annular wall of an annular groove or relief formed in the body's lower surface. A peripheral skirt or slinger preferably extends downwardly and outwardly from the tool's lower portion, and an inner surface of the slinger forms the outer wall of the groove. The tool is preferably a cup whose upper section defines a pocket which receives cleaning abrasives. The cup is made of a flexible rubber, preferably with some abrasive material therein.

The tool of the invention is used with a prophylaxis angle. The angle includes a hollow sleeve with a hollow head at an end of the sleeve. An upwardly extending driven gear is rotatably received in the head to be driven by a drive. The driven gear includes an upwardly opening threaded bore. A cap is placed on the head to maintain the driven gear in the head. The cap includes an upwardly extending stem through which the driven gear extends. Preferably, the free upper end of the cap stem has an external beveled surface which forms a knife edge.

The threaded shaft on the tool or cup is received in the threaded bore of the driven gear to secure the cup to the angle. When the tool is threaded into the driven gear and the driven gear rotates, the upper edges of the angle's cap acts as a knife to cut into the ring to form a lip. The annular groove permits the lip to expand outwardly, thereby reducing compression of the rubber outboard of the cap. This arrangement therefore creates a rotational seal between the lip and the cap stem.

Unlike the TRIPLE SEAL® cup of FIG. 1, the cup of the present invention has only one direct seal with the cap. Further, this seal is not a compression seal as was used with the prior art cup. This substantially reduces the amount of friction produced by the cap seal, allowing the cup to be driven with lower torques and reduces the amount of heat generated by operation of the cup. As can be appreciated, this benefits both the motor which drives the cup and the patient. Further, because the ring is separated from the bulk of the cup body by the relief, the ring is not affected by bending of the cup. Thus, the ring will stay in contact with the cap stem and the seal will be maintained throughout the use of the cup, even when the cup is distorted.

DESCRIPTION OF THE PREFERRED EMBODIMENT

Figure 3:
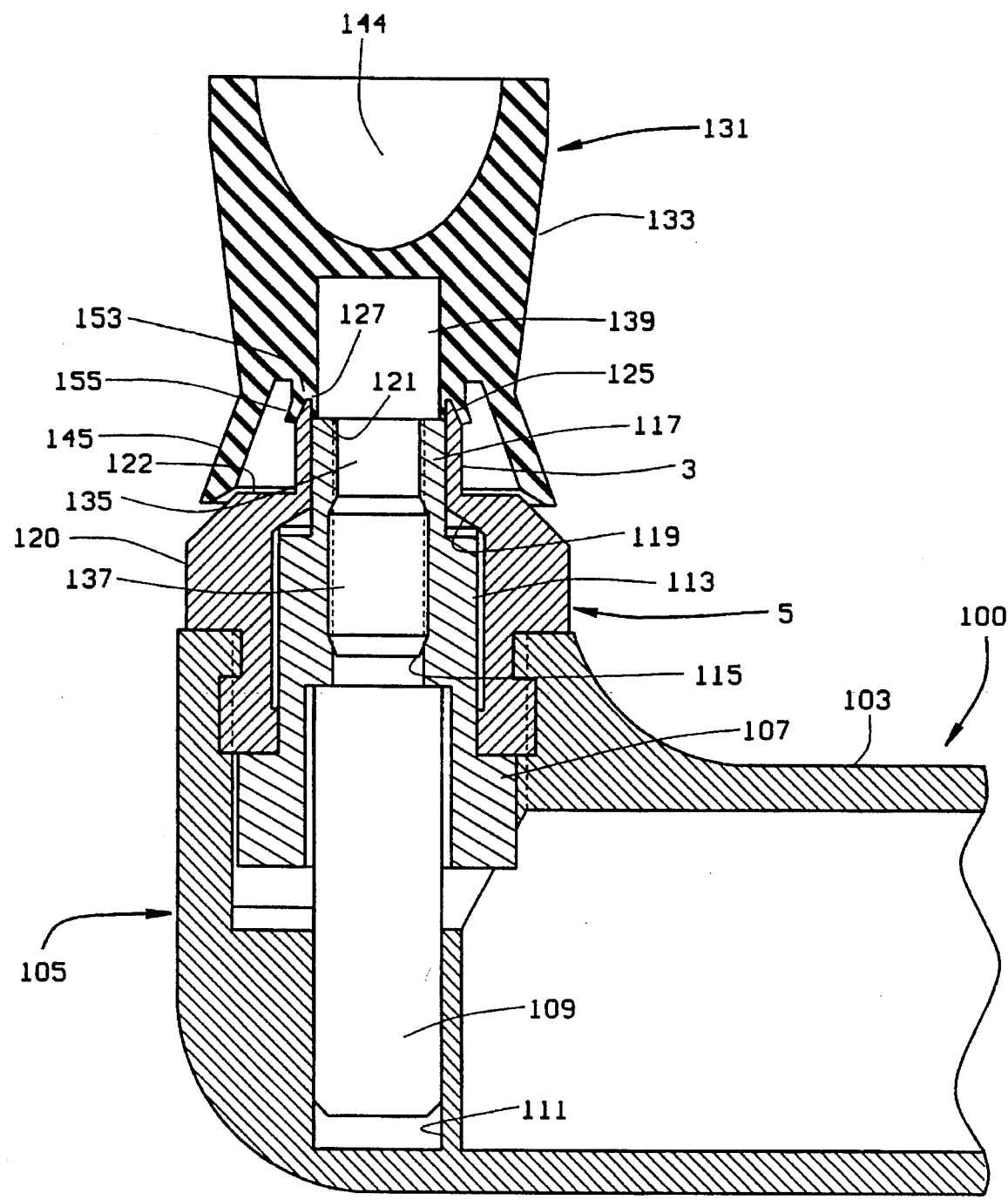
FIG. 3 is a cross-sectional view of the prophy cup of FIG. 2 applied to a prophy angle.

A conventional prophy angle head 105 is shown in FIG. 3. The head 105 includes a cap part 5 having a stem part 3 identical with those of FIG. 1. Angle head 105 includes a sleeve 100 which carries a drive gear, not shown. The sleeve is fitted over a handpiece, such as a Doriot, which drives the drive gear, as is known in the art. A driven gear 107 is rotatably mounted in head 105 to be in meshing contact with the drive gear. A shaft 109 is press fit into a bore 111 formed at the bottom of head 105. Driven gear 107 is rotatably mounted on shaft 109, and shaft 109 defines a thrust bearing for the driven gear. A boss 113, having an internally threaded bore 115, extends upwardly from gear 107. Boss 113 is stepped to define a narrower upper section 117.

Cap 5 is threaded to head 105 to secure the driven gear 107 in head 105. Cap 5 surrounds boss 113 and narrows at the junction 119 between the cap stem 3 and the main body 120 of the cap. The inner surfaces of the cap 5 thus define journal bearings for the driven gear 107 to prevent it from wobbling in the cap. As seen, cap body 120 has a generally flat upper surface 122 below stem 3. Upper portion 117 of gear 107 extends through cap stem 3. Portion 117, however, preferably does not extend the full extent of stem 3, and defines a seat 121 at the top surface of driven gear 113.

Stem 3 of the cap has a beveled top outer surface 125, extending downwardly and away from a sharpened annular top edge 127 of the stem.

A prophy cup 131 of the present invention is secured to angle 100 to be driven thereby. Cup 131 is made of a flexible or pliable elastomer. Suitable materials are known in the art, preferably having a Durometer hardness of about 40 to 70. Preferably, cup 131 is made from a natural rubber which includes a small amount of mild abrasive.

Figure 2:
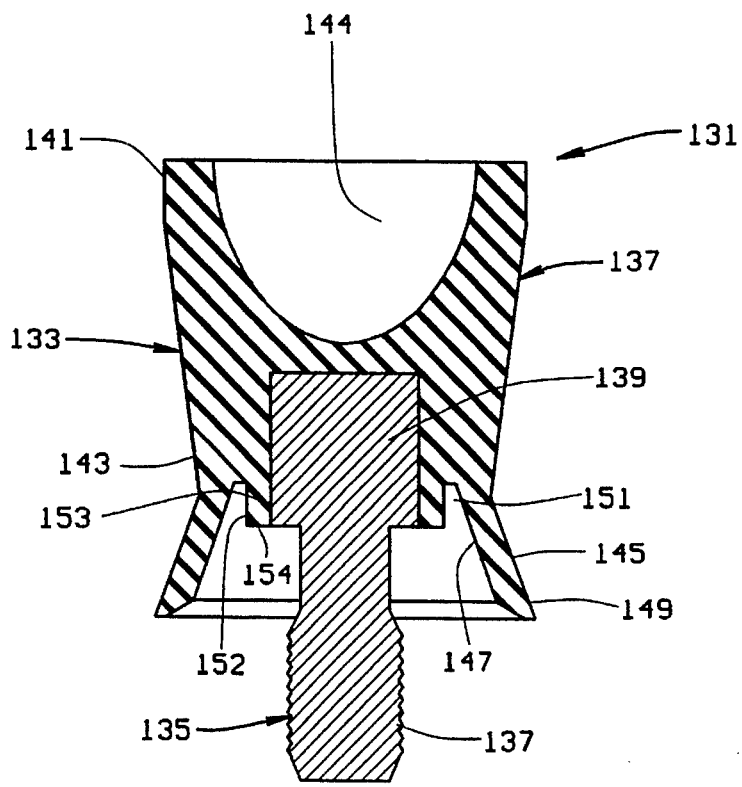
FIG. 2 is a cross-sectional view of a prophy cup of the present invention.

As shown in FIG. 2, cup 131 has a body 133 and a threaded shaft or screw 135. Shaft 135 has a threaded section 137 which is received in bore 115 of gear boss 113 to secure the cup to the angle head. Shaft 135 also has a head 139 about which cup body 133 is formed. The rubber cup is preferably vulcanized to the head 139, so that the shaft and body of cup 131 form an integral assembly.

Cup body 133 includes an upper portion 141 and a lower portion 143. A bowl 144 is formed in upper portion 141 to hold prophy paste. The lower portion 143 extends to the bottom of the shaft head 139 and includes the sealing elements of the cup. A peripheral skirt or slinger 145 extends downwardly and away from shaft 135. Slinger 145 has an inner surface 147 and an outer surface 149. Inner surface 147 extends upwardly into the body lower portion 143 to define the outer wall of a groove or relief 151. An annular inner wall 152 of the relief 151 defines a flexible annular ring 153 which surrounds shaft head 139. Because cup 131 is made from pliable or flexible rubber, the lower face 154 of the ring 153 may be cut into by the sharpened annular edge 127 to form a flexible ring seal therewith.

Turning to FIG. 3, when cup 131 is secured to angle head 105, ring 153 forms a ring seal with cap stem 3. When the cup 131 is screwed into the driven gear bore 115, edge 127 cuts into the ring 153 to form the ring seal, as seen in FIG. 3. As seeen in FIG. 3, the outer portion of the ring 153 forms a flexible lip 155 which is deflected outwardly into the recess 151, thereby reducing compression of the rubber and reducing the effort required to rotate the cup 131. This seal is the only seal between the cup and the angle head. The compression seal of the prior art cup is eliminated, as is the rib 7. The elimination of the compression seal and the rib seal reduces the friction created between the cup and the cap stem.

As shown, the slinger or skirt 145 has a diameter at its bottom slightly larger than the top, generally horizontal surface 122 of cap body 120. Slinger 145 will thus serve to direct abrasives and fluids away from the cap 5 and the ring seal. The slinger 145 is preferably thin so that it may easily be deflected should it contact the cap 5 during a prophylaxis procedure. This will allow the slinger to slide more easily over the cap, reducing friction and heat generated by the operation of the angle. Further, the thinness of the slinger will tend to reduce irritation of a patient's gums or cheeks, should the slinger contact the gum or cheek during the procedure.

In operation, the lip 155 of ring 153 closes against cap stem 3 to prevent any foreign materials from entering cap stem 117 and hence angle head 105. Slinger 145 facilitates operation of the seal by urging material away from the ring seal area. In tests, cup 131 was operated at speeds of between 1200 to 1500 rpm. When compression loads and side loads similar to those exerted upon the cup in a prophy procedure were applied to the cup, no material entered the angle. The relief 151 separates the ring seal 153 from the bulk of the cup body and moves the bending moment of the cup upwardly. Thus when side loads are placed on the cup, the ring will not separate from the cap stem, and the seal between the cap stem and the cup ring will be maintained. Thus, the cup seals the cap even when it is distorted by side loads.

Figure 1:
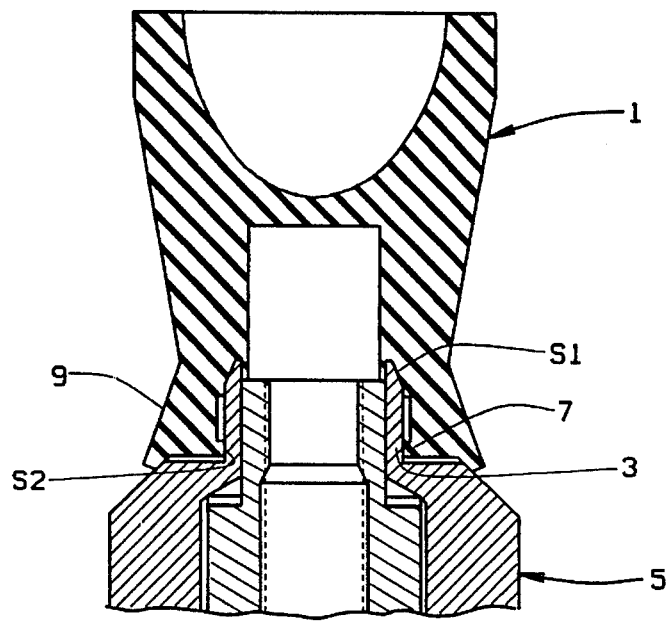
FIG. 1 is a cross-sectional view of a prior art prophy cup applied to a prophy angle.

Further, because the amount of friction created between the cup and the cap has been greatly reduced, less torque was needed on the part of the motor to drive the cup at the same or similar speeds, as compared to the cup of FIG. 1.

As can be appreciated, cup 131 seals the angle head 105 against abrasive paste and other material which could damage the angle if it were to enter the angle. This seal is maintained even when the cup is distorted. The sealing is accomplished with a minimum amount of friction between the cup and the cap, allowing the drive to operated at a lower torque requirements and for the angle head to operate substantially cooler than the prior art TRIPLE SEAL® prophy cup.

The foregoing description is intended to be illustrative and not limiting. Variations, within the scope of the appended claims, will be apparent to those skilled in the art. For example, a prophylaxis brush or other tool for use on the prophy angle can be provided with the seal of the present invention. Although the cup is preferably made of rubber, other elastomers may also be used. Although the peripheral slinger adds some protection, it is possible to eliminate it, thereby defining the sealing ring of the present invention merely by an upwardly extending annular wall having a diameter no more than about 1.3 times the diameter of the knife edge of the cap stem on the prophy angle, preferably less than 1.2 times the diameter of the stem edge. In all cases, the side wall of the sealing ring must extend upward a distance at least equal to the depth to which the cup stem cuts into the ring, in order to provide adequate flexibility of the lip 153. The shaft 109 could be integral with the driven gear of the prophy angle. These examples are merely illustrative.

I claim:

1. In combination a prophylaxis tool and a dental prophylaxis angle;

the angle including a hollow head, a hollow sleeve extending from said head, an upwardly extending driven member rotatably received in said head, means for driving said driven member received in said sleeve, an upwardly extending stem on said head having an annular knife edge, said driven member having a boss extending into said stem;

said tool including a body having an upper section, a lower section, a shaft which is received in said driven gear to secure said tool to said angle; said body lower section having a deformable annular ring concentric with said tool shaft, said annular knife edge of said stem cutting into a bottom edge of said ring to form a ring seal with said stem, said ring having a diameter no greater than 1.3 times the diameter of said annular edge of said stem.

2. The combination of claim 1 wherein said ring has a diameter less than 1.2 times the diameter of said annular edge of said stem.

3. The combination of claim 1 wherein shaft has a head, said head being received in said cup body lower portion, said knife edge being radially spaced from said head when said seal is formed.

4. In combination a prophylaxis tool and a dental prophylaxis angle;

the angle including a hollow head, a hollow sleeve extending from said head, an upwardly extending driven member rotatably received in said head, means for driving said driven member received in said sleeve, an upwardly extending stem on said head having an annular edge, said driven member having a boss extending into said stem;

said tool including a body having an upper section, a lower section, a shaft which is received in said driven gear to secure said tool to said angle; said body lower section having a deformable annular ring concentric with said tool shaft, said ring engaging said annular edge of said stem to form a ring seal with said stem, said ring having a diameter no greater than 1.3 times the diameter of said annular edge of said stem;

said stem having a beveled upper surface, said stem beveled surface cutting into a bottom edge of said ring to form a lip which seals against said stem and forms said ring seal.

5. The combination of claim 4 wherein said tool lower body has a lower surface, said ring being defined by a relief formed in said lower surface.

6. The combination of claim 5 including a slinger which extends downwardly and outwardly from said tool lower portion, said slinger having an inner surface and an outer surface, said slinger inner surface defining a radially outer surface of said relief.

7. The combination of claim 6 including means for maintaining said seal when said tool is deformed by side loads, said seal maintaining means including said relief, said relief radially separating said ring from said slinger such that the formed ring does not move with respect to said stem when side loads are applied to said tool, to maintain said seal.

8. The combination of claim 5 wherein said slinger is sufficiently thin to reduce irritation of a patient's gum or cheeks should the slinger contact said gum or cheeks during operational use.

9. The combination of claim 5 wherein said tool body is formed of pliable rubber.

10. The combination of claim 9 wherein said rubber includes abrasive material therein.

11. A dental prophylaxis angle including a head and a sleeve extending from said head, said head rotatably receiving a driven member and having a cap thereon to secure said driven member within said head; said cap including an upwardly extending stem having a sharp upper edge; said driven member extending partially through said cap stem; a prophylaxis cup being rotatably fixed to said driven member, said prophylaxis cup including a body, said cup body including an annular ring which is cut into by said sharp upper edge and forms a single ring seal with said cap stem to seal said cap stem against entry of foreign material into said dental angle, said ring seal being the only positive seal between said cup and said head, said annular ring being sufficiently narrow such that side loads applied to said cup will not break said ring seal.

12. The dental angle of claim 11 wherein said cup includes a slinger skirt surrounding said annular ring.

13. The dental angle of claim 12 wherein said cup includes a slinger which extends downwardly and outwardly from said cup lower portion, said slinger being radially spaced from said ring by a downwardly opening relief formed in said cup body lower portion, said slinger having an inner and an outer surface, said inner surface defining a radially outer surface of said relief, said ring defining at least a part of a radially inner surface of said relief.

14. A dental prophylaxis angle including a head and a sleeve extending from said head, said head rotatably receiving a driven member and having a cap thereon to secure said driven member within said head; said cap including an upwardly extending stem; said driven member extending at least partially through said cap stem; a prophylaxis cup being rotatably fixed to said driven member, said prophylaxis cup including a body, said cup body including an annular ring extending from a bottom of said cup, said ring engaging said cap stem to form a single ring seal with said cap stem to seal said cap stem against entry of foreign material into said dental angle; said cap stem having a beveled upper surface, said cap stem upper surface impaling said ring to form a ring which seals against said cap stem to form said ring seal.

15. The dental angle of claim 14 wherein said ring has an annular width sufficiently narrow so that the position of said ring with respect to said cap stem will not be substantially affected by side loads applied to said cup to maintain said seal when said cup is deformed.

16. A prophylaxis tool for use with a prophylaxis angle, said tool having a body and a screw, said body including an elastomeric lower portion, said screw including a head embedded in said lower portion of said body and a threaded section extending downwardly from said body; said lower portion having a lower surface substantially coplanar with a lower surface of said head, said lower surface of said lower portion abutting and surrounding said head, said lower surface of said lower portion being bounded by an upwardly extending annular wall to define an annular ring concentric with said threaded section of said screw.

17. The prophylaxis tool of claim 16 wherein said lower portion of said body includes a slinger skirt extending downwardly and outwardly, said slinger skirt including an inner surface spaced radially outwardly from said upwardly extending annular wall, said inner surface of said slinger skirt and said annular wall of said ring defining an upwardly extending relief.

18. The prophylaxis tool of claim 17 wherein said tool is a prophylaxis cup, said cup including a bowl formed in an upper portion of said elastomeric body.

19. The prophylaxis tool of claim 17 wherein said slinger skirt extends below said lower surface of said head of said screw.

20. The prophylaxis tool of claim 16 wherein the prophylaxis tool is a prophylaxis cup, the elastomeric body including an upwardly opening bowl for holding prophylaxis paste.

21. The prophylaxis tool of claim 16 wherein said ring has an annular width sufficiently narrow that the position of said lower surface of said ring will not be substantially affected by side loads applied to said cup to maintain said lower surface of said ring substantially coplanar with said lower surface of said head.

22. The prophylaxis tool of claim 16 wherein said annular ring is vulcanized to said head to form an integral assembly.

23. In the combination of a dental tool and a dental handpiece;

the handpiece including a housing, an annular stem on the housing, an outer surface of the stem being beveled to form an annular sharp free edge, a rotatable member rotatably received in the housing, the rotatable member having a boss extending into the stem, the boss forming a seat inside the stem;

the tool including a shaft which is received in the boss to mount the tool to the seat and an elastomeric body concentric with the tool shaft, the annular edge of the stem cutting into the elastomeric body to form a seal;

the improvement wherein the elastomeric body comprises an annular ring concentric with the shaft, the ring having a diameter sufficiently close to the diameter of the stem such that an outer portion of the annular ring forms a flexible lip, the flexible lip being deflected radially outward by the stem.

* * * * *